US010130672B2

(12) United States Patent
Sambanthamurthi et al.

(10) Patent No.: US 10,130,672 B2
(45) Date of Patent: Nov. 20, 2018

(54) ANTIVIRAL COMPOSITION

(71) Applicant: Malaysian Palm Oil Board, Kajang, Selangor (MY)

(72) Inventors: Ravigadevi Sambanthamurthi, Selangor Darul Ehsan (MY); Kalyana Sundram P. Manickam, Selangor Darul Ehsan (MY); Yew Ai Tan, Kuala Lumpur (MY); Mohd Basri bin Wahid, Selangor Darul Ehsan (MY)

(73) Assignee: Malaysian Palm Oil Board, Kajang (MY)

( * ) Notice: Subject to any disclaimer, the term of this patent is extended or adjusted under 35 U.S.C. 154(b) by 0 days.

(21) Appl. No.: 13/633,041

(22) Filed: Oct. 1, 2012

(65) Prior Publication Data

US 2013/0131158 A1    May 23, 2013

Related U.S. Application Data

(62) Division of application No. 12/670,398, filed as application No. PCT/MY2008/000075 on Jul. 23, 2008, now abandoned.

(30) Foreign Application Priority Data

Jul. 23, 2007  (MY) ................................ PI20071192

(51) Int. Cl.
| | | |
|---|---|---|
| *A61K 36/889* | (2006.01) | |
| *A61K 31/047* | (2006.01) | |
| *A61K 31/192* | (2006.01) | |
| *A61K 31/353* | (2006.01) | |

(52) U.S. Cl.
CPC .......... *A61K 36/889* (2013.01); *A61K 31/047* (2013.01); *A61K 31/192* (2013.01); *A61K 31/353* (2013.01)

(58) Field of Classification Search
None
See application file for complete search history.

(56) References Cited

U.S. PATENT DOCUMENTS 5,529,778 A    6/1996  Rohatgi
5,866,606 A *  2/1999  Schaller et al. ............. 514/547
2003/0031740 A1  2/2003  Sambanthamurthi et al.

FOREIGN PATENT DOCUMENTS

| WO | WO-9934812 A1 * | 7/1999 | ........... A61K 36/355 |
| WO | WO 0234072 A2 * | 5/2002 | ............... A23L 2/52 |
| WO | WO-0247703 A2 * | 6/2002 | ........... A61K 31/192 |
| WO | WO-2006/016363 | 2/2006 | |

OTHER PUBLICATIONS

MacPhillamy HB Plant Science Bulletin; A Publication of the Botanical Society of America, Inc. vol. 9, No. 2, Apr. 1963, 15 pages.*
Phillipson, J. New Drugs From Nature—It Could Be Yew; Phytotherapy Research 13 (1999) pp. 2-8.*
Raskin et al. Can an Apple a Day Keep the Doctor Away?; Current Pharmaceutical Design; 2004, 10, 3419-3429.*
Revilla et al. Comparison of Several Procedures Used for the Extraction of Anthocynains From Red Grapes; J. Agric. Food Chem. 1998, 46, pp. 4592-4597.*
Ahmad, K Herbal Treatment for HIV/AIDS Not Reccomended; Lancet Infectious Diseases; 5(9) 2005, p. 537.*
International Search Report dated Jan. 23, 2009 for International Application No. PCT/MY2008/000075, 2 pages.
Gu, et al, Dietary effect of tocopherols and tocotriols on the immune function of spleen and mesenteric lymph node lymphocytes in brown Norway rats, Biosci Biotechnol Biochem, (1999), 63(10):1697-1702.
Oil Palm, Wikipedia, archived to Apr. 20, 2005, URL,<http://web.archive.org/web/20050420071030/http://en.wikipedia.org/wiki/Oil_palm, Accessed May 21, 2012, 2 pages.
Sen, et al, Tocotriols: Vitamin E beyond tocopherols, Life Sciences, (2006), 78:2088-2098.
Sundram et al, Palm fruit chemistry and nutrition, Asia Pacific Journal of Clinical Nutrition, 12(3): 355-362, 2003.
Wattanapenpaiboon et al., Phytonutrient deficiency: the place of palm fruit. Asia Pacific Journal of Clinical Nutrition, 12(3): 363-368, 2003.
Balasundram et al., "Antioxidant properties of palm fruit extracts," Asia Pac J Clin Nutr., 2005, 4(4):319-324.

* cited by examiner

*Primary Examiner* — Amy L Clark
(74) *Attorney, Agent, or Firm* — Rahman LLC (57) ABSTRACT

The present invention relates to a composition of phenolic antioxidants obtained from oil palm, and more particularly this invention relates to a composition for promoting immunity in general and most essentially against Human Immunodeficiency Virus (HIV) related infections. Accordingly, the composition having the said oil palm compounds can effectively inhibit various viruses, further supporting oil palm compounds as one of the broad spectrum antiviral drugs.

7 Claims, 6 Drawing Sheets

ANTIVIRAL COMPOSITION

FIELD OF INVENTION

The present invention relates to a composition enriched but not confined, to phenolic antioxidants obtained from a botanical extract of oil palm vegetation liquor obtained from the palm oil milling process, and more particularly this invention relates to a composition for promoting immunity in general and most essentially against Human Immunodeficiency Virus (HIV) related infections.

BACKGROUND OF INVENTION

Over the past decade, scientific research has provided increasing evidence that crude extracts of plants may provide lead molecules in relation to drugs for a variety of critical ailments. Accordingly, substantial progress has been made in this regard in order to further determine and thus provide a natural origin solution to illnesses.

In plants, phenolics and flavonoids are the most abundant and ubiquitous products of secondary plant metabolism. Under normal circumstances, they are often used by plants as a defense mechanism against animal predation and the like. Additionally, recent studies have begun to examine and heighten the role of agriculture in the context of producing immunity against illnesses.

One of such numerous illnesses that can be regarded as the biggest challenge in the medical science field is AIDS which is widely known to be caused by the virus HIV [Human Immunodeficiency Virus], which relates to the disruption of the immune system. Evidently, many have lost their lives due to this illness. At present time, massive amount of research has been conducted to determine suitable drugs for the treatment of AIDS. Naturally, plant-derived medicines comprising phenolics and antioxidants are one of the most highly utilized categories of drugs and thus have been taken into account in the possibility of treating AIDS.

The HIV virus causing AIDS belongs to the retrovirus group of viruses. Retroviruses are widespread in nature and can be classified according to biological property, morphology and genome size. Retroviruses are characterized by the presence of the enzyme reverse transcriptase in the virions. Reverse transcriptase is required for the unique retroviral type of multiplication. After entering the cell, the uncoated viral RNA is transcribed to double stranded DNA which is then incorporated into the DNA of the host cell as a provirus. Reverse transcriptase is required for early proviral DNA synthesis and is therefore a prime target for anti-retroviral therapy including AIDS.

Prior art of similar purpose includes ayurvedic compositions, wherein they comprise pre-determined amount of plant extracts and compositions which consist of a combination of well known medicinal plants or herbs, for example ginseng, *Radix Astragali* and the like. Apart from the above, other solutions comprise pharmaceutically active compounds, having inhibitors.

Nevertheless, among these prior arts, more often than not, in the case where inhibitors are the main compounds, there are circumstances where the virus develop resistance against these inhibitors, and therefore will defeat the whole purpose of the compounds, in which this can be regarded as the main drawback in using inhibitors to disrupt further propagation of the said virus.

An exemplary of a composition which is related to the treatment of AIDS is as disclosed in U.S. Pat. No. 5,529, 778—Ayurvedic Composition for the Prophylaxis and Treatment of AIDS, Flu, TB and Other Immuno-Deficiencies and The Process Preparing the Same (Surendra Ruhatgi et al.) which suggests a composition containing the isolates and extracts of a variety of herbs, said herbs including Phyllantus niruri, Tinosfora cordifolia, phyllantus emblica, Terminalia beleria and Terminalia cherbulia. Accordingly, the said composition stimulates the physiological functions of the body for the treatment of AIDS. Evidently, the essential compound of this invention is the extracts or isolates from a plurality of herbs, which is distinctive from the essential compounds of the present invention.

Apart from the above, there have been numerous efforts and research conducted to seek for effective broad spectrum antiviral drugs. However, there have yet to be any antiviral drugs successfully developed for treating mixed viral infections which are as well non-toxic. Considering the appalling effect of mixed viral infections which therefore lead to AIDS, it is highly necessary to develop a non-toxic and effective broad spectrum antiviral drug.

In regards to plant derivatives, previous studies have revealed that coconut oils may provide the superiority function of antiviral effects. In accordance to their disclosures, the content of lauric acid which is formed into monolaurin in human or animal body may provide the ability to eliminate virus including HIV, herpes, cytomegalovirus, influenza and a variety of pathogenic bacteria.

Another eminent exemplary of a plant having extremely beneficial health properties is palm fruit. The oil palm contains compounds which can be considered as highly effective in the treatment of serious illnesses. Recent discoveries in regards to further beneficial health properties of phenolics and antioxidants which are eminently found in oil palm include providing treatments for cancer, and for eliminating skin problems.

The present invention provides a new approach in using oil palm, particularly in providing a treatment of AIDS by way of a composition that promotes immunity against HIV infection.

Consequently, primary object of the present invention to provide a composition based oh a botanical extract of oil palm vegetation liquor obtained from the palm oil milling process for promoting immunity against HIV virus infection and thus for treatment of AIDS.

It is a further object of the present invention to provide an improved composition and method for producing a broad spectrum antiviral which is non-toxic.

It is further the object of the present invention to provide an improved composition and formulation for producing a composition containing antioxidants and phenolics obtained from oil palm devoid of chemically prepared adverse drug reactions in a patient in need thereof.

It is a further object of the present invention to provide a composition and formulation for producing a composition containing but not limited to antioxidants and phenolics from botanical extract of oil palm vegetation liquor obtained from the palm oil milling process having anti-viral effects.

SUMMARY OF INVENTION

The present invention relates to an antiviral composition comprising antioxidants extracted from the vegetation liquor of the palm oil milling process for promoting immunity and for providing inhibition against HIV infections.

The composition of the present invention may be provided with pharmaceutically acceptable carriers.

Combination therapies involving HIV protease inhibitors and HIV reverse transcriptase inhibitors are the cornerstones of currently recommended therapies for HIV infection. In accordance with one embodiment of the present invention, the botanical extract of vegetation liquor from the palm oil milling process as well as its purified fractions have potent inhibitory action against both HIV protease and reverse transcriptase as well as hepatitis C (HCV) protease.

The present invention further relates to the use of therapeutically effective amount of a composition in the preparation of a medicament for promoting immunity and for providing inhibition against HIV and HCV infections in a patient in need thereof, wherein the composition may be administered orally or as supplements or with additives.

The term "phenolics" refers to a class of compounds grouped together due to their chemical structure wherein in this document is extracted from vegetation liquor of the palm oil milling process.

The term "flavonoids" refers to naturally occurring chemicals in plants, wherein in this document is extracted from vegetation liquor of the palm oil milling process.

DETAILED DESCRIPTION OF THE PRESENT INVENTION

As mentioned, the present invention provides a composition based on but not confined to the antioxidants and phenolics obtained from vegetation liquor of the palm oil milling process promoting immunity against HIV virus infection and thus for treatment of AIDS.

Accordingly, the present invention is to provide a broad spectrum antiviral composition which comprises but is not limited to antioxidants and phenolics obtained from vegetation liquor of the palm oil milling process. Essentially, the composition comprising antioxidants, phenolic acids and flavonoids and the usage of the said composition in a medicament for providing immunity against and thus treatment of mixed viral infections.

The preparation of composition formulations according to the present invention are described in detail by referring to the experimental examples. However, the present invention is not limited to these examples.

Methodology and Assay Design

Extraction

In accordance to a preferred embodiment of the present invention, the method and preparation of the antiviral composition comprise the steps of isolating the main compounds. The main compounds or extract of the composition of the present invention can be prepared in a variety of appropriate ways, however should not be considered as limiting the scope of invention, but merely as being illustrative. The isolated extracts mainly comprise phenolic compounds, fruit acids, fruit sugars and glycerol from the vegetation liquor from the palm oil milling process and the prepared formulations containing these extracts. Isolation methods include, and not limiting to, filtration, distillation, crystallization and flash column chromatography. The main requirement for the isolation is highly pure and concentrated samples. The preferred isolation method in accordance to the present invention is membrane filtration employing molecular weight cut-off sieves. The resultant filtrate (botanical extract) is further separated using flash column chromatography.

The said isolation method may consist of extracting the crude oil palm product, with a predetermined yield rate.

The biologically active extracts of palm vegetation liquor useful in this invention can be prepared by any means capable of extracting phenolic compounds from the vegetation liquor using standard extraction techniques or techniques as described in US Patent Application No. 20030031740 (Sambanthamurthi, Tan and Sundram 2004). Such extractions include but are not limited to ethanol, methanol, acetone, ethyl acetate and butanol.

In addition to direct use of an extract, it is also possible to use different fractions of the oil palm phenolic compounds. What constitutes an effective amount of an extract, or an active portion thereof, will depend on the purity of the extract.

Figure 2:
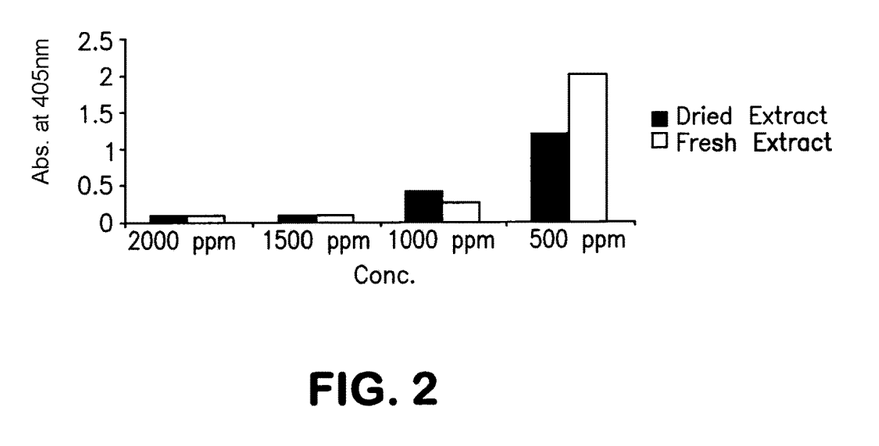
FIG. 2 shows a bar graph of reverse transcriptase activity at various concentrations of botanical extract from the vegetation liquor of the palm oil milling process. Concentrations refer to gallic acid equivalent.

In accordance to the present invention, and for the purpose of comparison, the preparations of extracts are preferably in the liquid and dried forms as shown in FIG. 2 of the present invention.

Methodologies

Methodology-Flash Chromatography

The botanical extract of oil palm vegetation liquor obtained from the palm oil milling process as described in US Patent Application No. 20030031740 (Sambanthamurthi, Tan and Sundram 2004) were partially purified using flash chromatography and preparatory high pressure liquid chromatography using among others an Advanced Protein Purification System purchased from Waters, USA). The extract was injected into a column and then eluted with a methanol gradient, ranging from 0% to 100%. The phenolic compounds were eluted in accordance with their solubility in methanol.

Samples from different pooled fractions were concentrated using a vacuum concentrator (Oligo Prep model OP120 purchased from Savant, USA) before being analysed for activity.

Detailed Flash Chromatography Method

Figure 1:
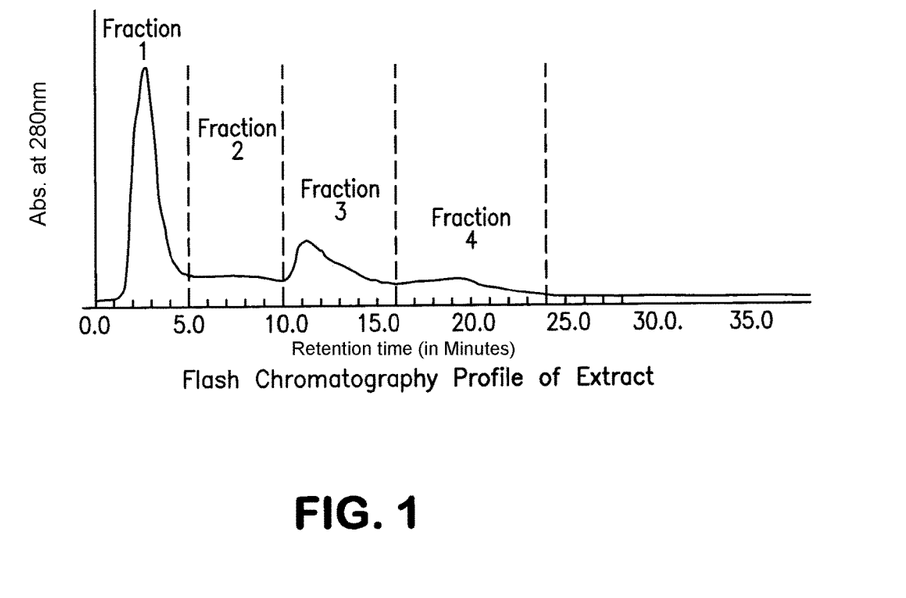
FIG. 1 shows a flash chromatography profile of phenolic content from palm oil extract samples expressed as μg gallic acid equivalent (GAE) per mL of sample or in parts per million (ppm) GAE.

Four mL of extract were injected into a flash column (C18; 20 g/70 ml purchased from Jones Chromatography, USA). The flow rate was set at 5 mL/min. The column was eluted with water for 5 min. Then, a linear gradient of methanol (0-100%) was applied for 25 min. The column was eluted a further 5 min with 100% methanol to ensure the complete removal of the sample from the column. The eluates were collected in test tubes (2.5 mL in each test tube) and assayed for phenolic content. The phenolic content in the samples were expressed as µg gallic acid equivalent (GAE) per mL of sample or in parts per million (ppm) GAE. The eluates were pooled into four fractions as shown in FIG. 1.

Methodology-Reverse Transcriptase Assay: Inhibitor Determination The preferred assay system for analyzing the human immunodeficiency virus (HIV) replication activity for particle associated in accordance to the present invention is the Reverse Transcriptase system. According to studies in the relevant field, the viral activity can be determined by way of a Reverse Transcriptase Assay. Inhibition of reverse transcriptase is thus indicative of anti-viral and more specifically anti-HIV activity when HIV reverse trancriptase is used in the assay.

Two different commercial Reverse Transcriptase Assay Kits were used to confirm the anti-HIV properties of the botanical extract of oil palm vegetation liquor obtained from the palm oil milling process.

Roche™ Reverse Transcriptase Assay, Colorimetric

This is a colorimetric enzyme immunoassay for the quantitative determination of retroviral reverse transcriptase activity by incorporation of dioxigenein- and biotin-labeled dUTP into DNA. The Reverse Transcriptase Assay, colorimetric takes advantage of the ability of reverse transcriptase to synthesize DNA, starting from the template/primer hybrid poly (A)×oligo (dT)15. Digoxigenin- and biotin-labeled nucleotides in an optimized ratio are incorporated into one and the same DNA molecule, which is freshly synthesized by the RT. The detection and quantification of synthesized DNA as a parameter for RT activity follows a sandwich ELISA protocol: Biotin-labeled DNA binds to the surface of microtiter plate (MTP) modules that have been precoated with streptavidin. In the next step, an antibody to digoxigenin, conjugated to peroxidase (anti-DIG-POD), binds to the digoxigenin-labeled DNA. In the final step, the peroxidase substrate ABTS is added. The peroxidase enzyme catalyzes the cleavage of the substrate, producing a colored reaction product. The absorbance of the samples can be determined using a microtiter plate (ELISA) reader and is directly correlated to the level of RT activity in the sample. For quantification of the inhibitory effect of the botanical extract, a reverse transcriptase, HIV-1 recombinant was used in conjunction with the Reverse Transcriptase Assay, Colorimetric. The assay was carried out according to manufacturers' instructions. (Cat. No. 1468 120)

Accordingly, the extract was prepared at various concentrations in both the dried and aqueous form. The four fractions from flash chromatography were also prepared with varying concentrations. Referring to FIG. 2 of the present invention, both the dried and aqueous extracts exhibited significant inhibitory action against HIV-1 reverse trancriptase. The activity was dose-dependent with both the dried and aqueous extracts at 1500 ppm gallic acid equivalent exhibiting more than 90% inhibition in activity as seen by the decrease in absorbance at these concentrations.

Figure 3A:
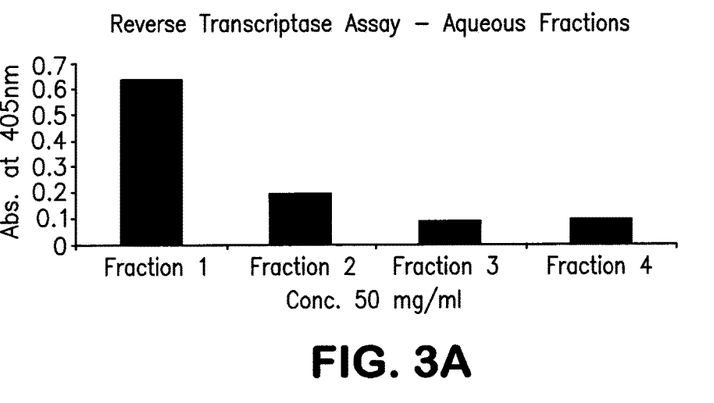
FIG. 3A shows a bar graph of reverse transcriptase activity of various fractions of oil palm phenolic-rich extracts.

The inhibitory action of the four fractions from flash chromatography is shown in FIG. 3A. Fractions 3 and 4 showed the highest inhibitory effect. These fractions are high in cinnamates and catechin. Fraction 2 which is rich p-hydroxybenzoic acid also showed significant inhibitory effect.

Figure 3B:
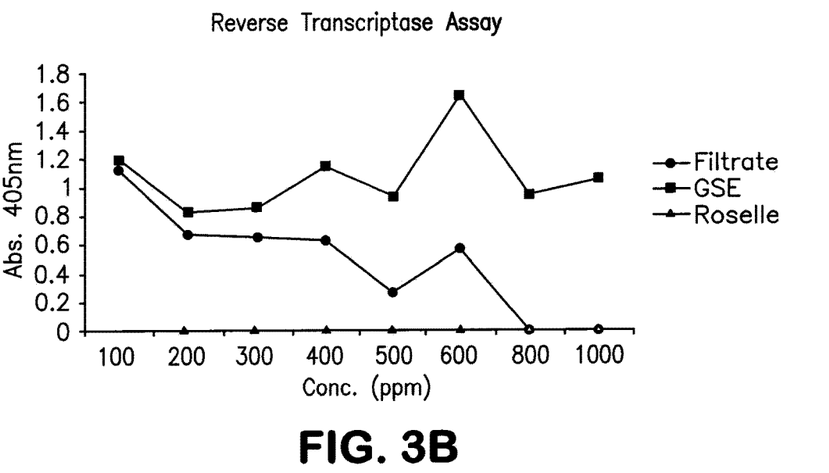
FIG. 3B shows a graph of reverse transcriptase activity with oil palm and other phenolic extracts, such as roselle and grape seed extract (GSE).

The inhibitory effect of oil palm extract was compared with other phenolic extracts such as roselle and grape seed extract (GSE). The results are shown in FIG. 3B. Grape seed extract did not have any inhibitory effect on reverse transcriptase activity. Roselle however showed activity at 200 ppm gallic acid equivalent.

Molecular Probes EnzChek® Reverse Transcriptase Assay Kit (E-22064)

Molecular Probes EnzChek ® Reverse Transcriptase Assay uses Pico Green dsDNA quantitation reagent which preferentially detects dsDNA or RNA-DNA heteroduplexes over single-stranded nucleic acids or free nucleotides. In this assay reverse trancriptase generates long RNA-DNA heteroduplexes from a mixture of a long poly (A) template, an oligo-dT primer and DTTP. The RNA-DNA heteroduplexes formed are then detected by the PicoGreen reagent. For determining inhibitory action against reverse transcriptase activity, a fixed amount of reverse transcriptase is incorporated in the assay and the reduction in activity quantified. The detailed experimental protocol was carried out according to manufacturer's instructions.

Figure 3C:
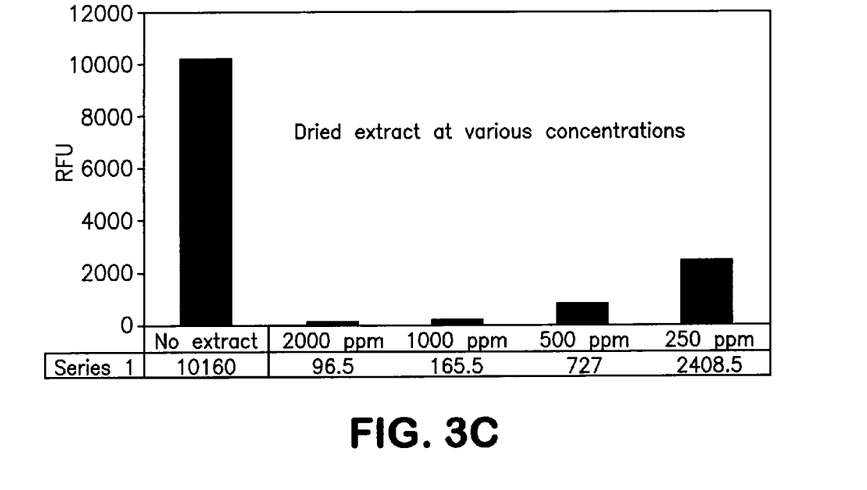
FIG. 3C shows a graph of reverse transcriptase activity at various concentrations of oil palm phenolic extracts using Molecular Probes EnzChek® Reverse Transcriptase Assay Kit.
Figure 4A:
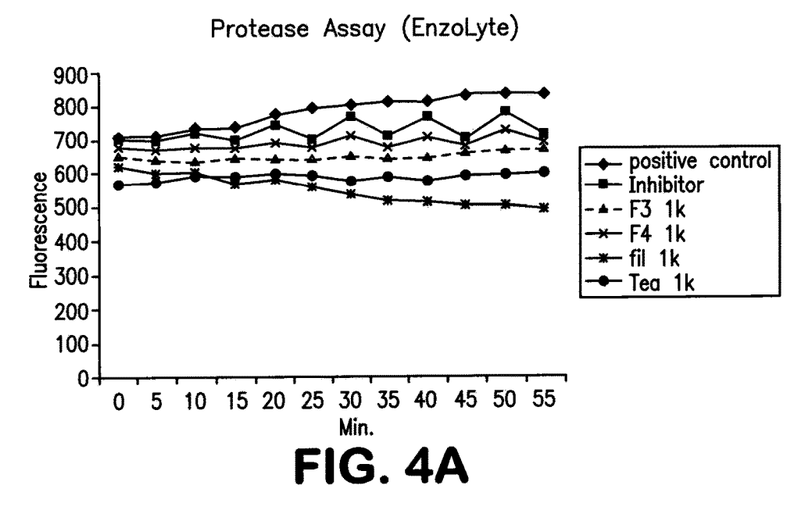
FIG. 4A shows a graph of protease activity of Hepatitis C Virus NS3/4A protease in the presence of botanical extract of oil palm milling process (fil 1K), Fractions 3 and 4, and a commecial preparation of black tea, all at concentrations of 1000 ppm stock solution.
Figure 4B:
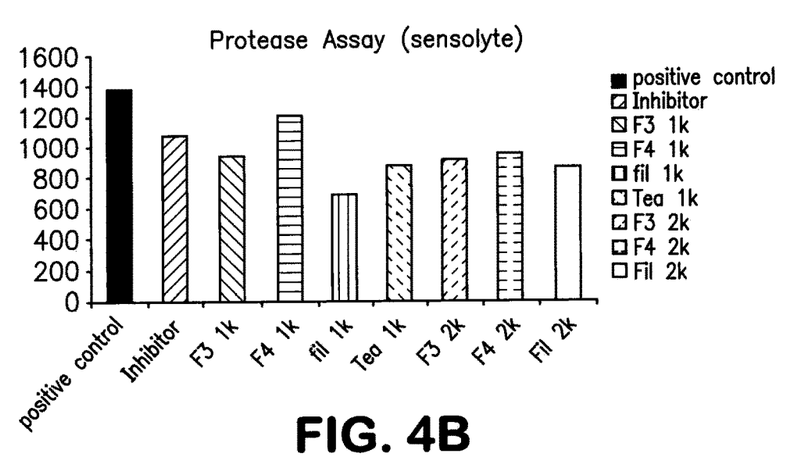
FIG. 4B shows a graph of protease activity of Hepatitis C Virus NS3/4A protease in the presence of botanical extract of oil palm milling process (fil 1K), Fractions 3 and 4, and a commecial preparation of black tea, at concentrations of 1000 (1k) or 2000 (2k) ppm stock solution. Positive control refers to protease assay without any inhibitors.

The results using this method (shown in FIG. 3C) again showed potent inhibitory action against reverse transcriptase activity. At 1000 ppm gallic acid equivalent, reverse transcriptase activity was almost completely inhibited. Even with the concentration as low as 250 ppm has exhibited about 80% inhibition of reverse transcriptase activity.

In virus systems, proteases are enzymes that aid in the maturation of other viral proteins, making them functional. For example without the work or protease, HIV will not mature properly and therefore will not be able to make copies of itself and infect other cells. This is also true for other virus Such as the Hepatitis C virus (HCV).

Inhibition of protease activity is indicative of anti-viral activity. Protease Inhibitors are medications that block the functioning of the enzyme protease. Without functioning protease, HIV and HCV are unable to mature and therefore cannot make more copies of themselves thus lowering the viral loads carried by AIDS and HCV patients.

Three different commercial Protease Assay Kits were used to confirm the antiviral properties of the botanical extract of oil palm vegetation liquor obtained from the palm oil milling process.

EnzoLyte™ 620 HCV Protease Assay

The EnzoLyte™ 620 HCV Protease Assay kit which is optimized for detecting the activity of hepatitis C virus NS3/4A protease was used to test the inhibitory effect of the extract. The NS3/4A protease of hepatitis C virus (HCV) is required for the cleavage of viral nonstructural polyprotein at the NS3-NS4A, NS4A-NS4B, NS4B-NS5A sites. Three cleavage sites are essential for the maturation of the viral proteins. This protease is one of the key targets for developing anti-HCV drugs.

The kit utilized a HiLyte Fluor™ TR/QXL™610 fluorescence resonance energy transfer (FRET) peptide substrate which could be monitored at Ex/Em=591 nm/622 nm upon proteolytic cleavage. The FRET peptide was derived from the cleavage site of NS4A/NS4B. In the FRET peptide, the fluorescence of HiLye Fluor™ was quenched by QXL™ 610. Upon cleavage into two separate fragments by the HCV NS3/4A protease, the fluorescence of HiLyteFluor™ was recovered and monitored at excitation/emission=591/622. Inhibitors would thus reduce the fluorescence.

The detailed experimental protocol was carried out according to manufacturer's instructions.

All the extracts showed significantly higher protease inhibitory action compared to even the commercial inhibitor (inhibitor) supplied with the kit.

The SensoLyte™ 520 HIV Protease Assay

The SensoLyte™ 520 HIV Assay kit used a new FRET peptide substrate that incorporated HiLyte Fluor™ 488 (fluorophore) and QXL™ 520 (quencher) for measurement of enzyme activities. In the intact FRET peptide, the fluorescence of HiLyte Fluor™ 488 was quenched by QXL™ 520. Upon cleavage of the FRET peptide by HIV protease, the fluorescence of HiLyte Fluor™ 488 was recovered and monitored at excitation/emission=490 nm/520 nm.

The detailed experimental protocol was carried out according to manufacturer's instructions.

As in the HCV protease assay, the botanical extract of vegetation liquor from the palm oil milling process showed significantly higher inhibitory action against HIV protease.

EnzChek Protease Assay

The Molecular Probes' EnzChek Protease Assay Kit was used to further test for protease inhibitory action of oil palm extracts. The kit used a fluorescence-based assay for detecting metallo-, serine and sulfydryl proteases. It contained casein derivatives which were heavily labeled with the pH-insensitive green fluorescent BODIPY FL or red-fluorescent BODIPY TR-X dyes resulting in almost total quenching of the conjugate's fluorescence. Protease-catalysed hydrolysis released highly fluorescent BODIPY FL or BODIPY TR-X dye-labeled peptides. The accompanying increase in fluorescence was measured in a microplate reader. Inhibitors thus would decrease the fluorescence. The inhibitory action of botanical extracts of vegetation liquor of the palm oil milling process as well as partially purified fractions on various proteases including but not confined to chymotrypsin (serine protease). Pepsin (acid protease) Elastase (metalloprotease) was investigated using the EnzChek Protease Assay.

The detailed experimental protocol was carried out according to manufacturer's instructions.

Figure 5A:
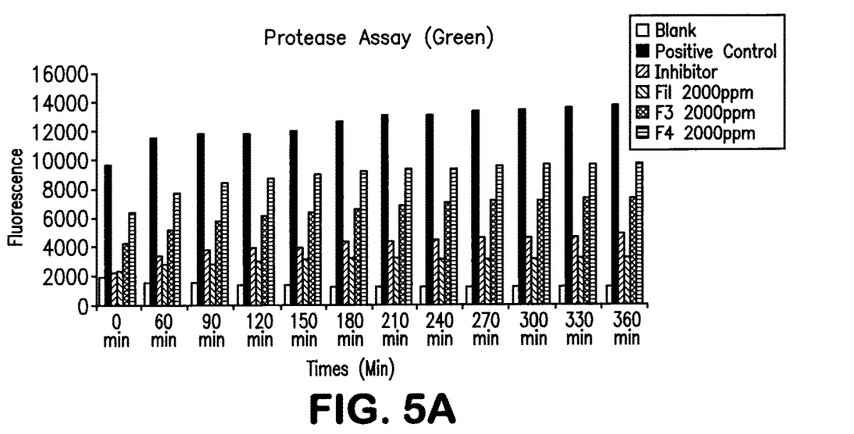
FIG. 5A shows a graph of protease activity in the presence of botanical extract of oil palm milling process (fil 2000 ppm), Fraction 3 (F31k) and Fraction 4 (F41k), all at concentrations of 2000 (2k) ppm stock solution. Positive control refers to protease assay without any inhibitors. Inhibitor refers to the commercial inhibitor provided with the kit (Molecular Probes' EnzChek Protease Assay Kit®).
Figure 5B:
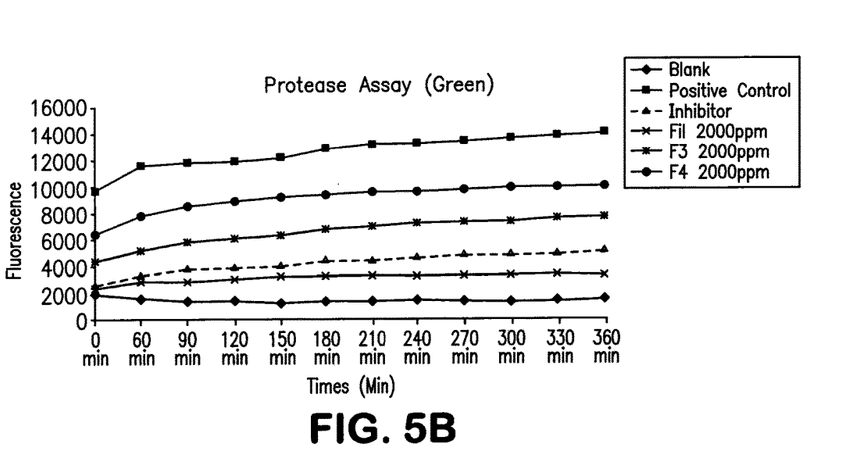
FIG. 5B shows a graph of protease activity in the presence of botanical extract of oil palm milling process (fil 2000 ppm), Fraction 3 (F31k) and Fraction 4 (F41k), all at concentrations of 2000 (2k) ppm stock solution. Positive control refers to protease assay without any inhibitors. Inhibitor refers to the commercial inhibitor provided with the kit (Molecular Probes' EnzChek Protease Assay Kit®).

In all cases significant inhibitory action was observed and FIG. 5 shows the results obtained using the protease chymotrypsin and casein derivative labeled with green fluorescent BOOIPY FL dye as substrate.

The botanical extract of palm and the partially purified fractions showed significantly higher protease inhibitory action compared to even the commercial inhibitor (inhibitor) supplied with the kit.

The conducted experiments using five different methodologies have shown that the compositions having but not confined to the said oil palm phenolic compounds can effectively inhibit various viruses, further supporting oil palm compounds as one of the broad spectrum antiviral drugs. The results also indicate that roselle and tea extracts also possess inhibitory action against reverse transcriptase suggesting that the extracts from palm can be used on their own or in combination with roselle and tea extracts for anti-viral function. Current HIV and HCV therapies are often contraindicated or poorly tolerated, underscoring the need for safer and more effective drugs. The botanical extracts of vegetation liquor of the palm oil milling process as well as partially purified fractions showed potent inhibition against HIV reverse transcriptase and protease and HCV protease in vitro and hence are potentially useful for development of future antiviral therapies including hepatitis C virus (HCV) therapies.

Dosage and Administration

In accordance to a preferred embodiment of the present invention, the compounds of the present invention may be formulated in a wide variety of oral administration dosage form and carriers. It can be in the form of tablets, capsules, solutions, emulsions, syrups or suspensions. Nevertheless, composition of the present invention may be efficacious when used together with one or more additives in conventional proportions.

The foregoing invention has been described in some detail by way of examples; however it will be obvious to one skilled in that changes and modifications may be practiced within the scope of the appended claims.

The invention claimed is:

1. A method for inhibiting HIV viral protease or reverse transcriptase activity in a subject infected with HIV, the method comprising orally administering to said subject a purified fraction of a methanol extract of an oil palm vegetation liquor obtained from a palm of milling process, wherein the fraction is administered to the subject in an amount effective to inhibit the HIV viral protease or reverse transcriptase activity, wherein said fraction is obtained from the vegetation liquor using flash chromatography with a gradient elution of water, 0-100% methanol and 100% methanol, and wherein said fraction comprises phenolic compounds.

2. The method of claim 1, wherein administration of the fraction at least partially inhibits replication of HIV in the subject.

3. The method of claim 1, wherein the fraction is combined with a pharmaceutically acceptable carrier.

4. The method of claim 1, wherein the fraction is administered in combination with one or more extracts selected from the group consisting of roselle extract and tea extract.

5. An in vitro method for inhibiting HIV viral protease or reverse transcriptase activity in a cell infected with HIV, the method comprising contacting said cell with a purified fraction of a methanol extract of an oil palm vegetation liquor obtained from a palm oil milling process, wherein the fraction is contacted with the cell in an amount effective to inhibit the HIV viral protease or reverse transcriptase activity, wherein said fraction is obtained from the vegetation liquor using flash chromatography with a gradient elution of water, 0-100% methanol and 100% methanol, and wherein said fraction comprises phenolic compounds.

6. The method of claim 1, wherein the fraction is obtained by flash chromatography using a C18 flash column, wherein a flow rate of the chromatography is 5 mL/min and the gradient elution is of water at 0 minute to 5 minutes followed by a linear gradient of 0-100% methanol for 25 minutes followed by 100% methanol for 5 minutes.

7. The method of claim 5, wherein the fraction is obtained by flash chromatography using a C18 flash column, wherein a flow rate of the chromatography is 5 mL/min and a gradient elution is water at 0 minute to 5 minutes followed by a linear gradient of 0-100% methanol for 25 minutes followed by 100% methanol for 5 minutes.

* * * * *